United States Patent [19]

Tanaka et al.

[11] Patent Number: 4,908,451

[45] Date of Patent: Mar. 13, 1990

[54] PROCESS FOR PREPARING α-SUBSTITUTED CARBONYL COMPOUND

[75] Inventors: Masato Tanaka; Toshiyasu Sakakura, both of Ibaraki, Japan

[73] Assignee: Agency of Industrial Science and Technology, Tokyo, Japan

[21] Appl. No.: 172,155

[22] Filed: Mar. 23, 1988

Related U.S. Application Data

[62] Division of Ser. No. 883,808, Jul. 7, 1986, Pat. No. 4,772,714.

[30] Foreign Application Priority Data

Jul. 8, 1985 [JP] Japan ................................ 60-149727
Jul. 8, 1985 [JP] Japan ................................ 60-149728
Jul. 8, 1985 [JP] Japan ................................ 60-149729

[51] Int. Cl.$^4$ .................. C07D 401/00; C07D 409/00; C07D 411/00; C07D 211/72
[52] U.S. Cl. ..................................... 546/267; 546/283; 546/284; 546/280; 546/306; 546/332; 549/60; 549/68; 549/76; 549/449; 549/451; 548/204; 548/495; 548/467; 560/34; 560/169
[58] Field of Search ............... 546/267, 283, 284, 280, 546/306, 332; 549/60, 68, 76, 449, 451; 548/204, 495, 467; 560/34, 169

[56] References Cited

U.S. PATENT DOCUMENTS 4,556,717 12/1985 Wetter et al. ................... 560/34

OTHER PUBLICATIONS

March, "Advanced Organic Chemistry", McGraw-Hill, New York, NY, 1968, p. 460.
*Organic Reactions,* vol. 10, pp. 143-156, 1959.

*Primary Examiner*—Mary C. Lee
*Assistant Examiner*—Robert C. Whittenbaugh
*Attorney, Agent, or Firm*—Armstrong, Nikaido, Marmelstein, Kubovcik & Murray

[57] ABSTRACT

A process is disclosed for the preparation of α-substituted carbonyl compounds, wherein α-substituted ketone is prepared by the following reaction:

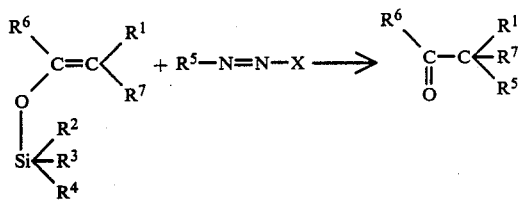

α-azo ester is prepared by the following reaction:

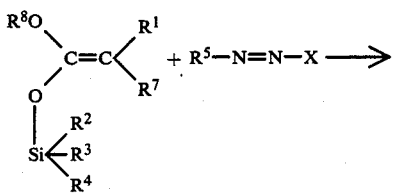

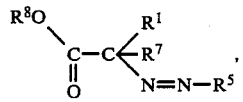

and α-hydrozono ester is prepared by the following reaction:

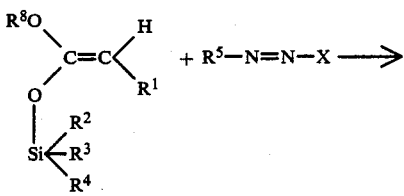

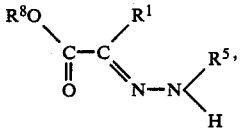

wherein the α-azo ester and α-hydrazono ester obtained by the above reactions include novel compounds, which are also disclosed.

6 Claims, No Drawings

PROCESS FOR PREPARING α-SUBSTITUTED CARBONYL COMPOUND

This application is a divisional of application Ser. No. 883,808 filed 7/7/86, now U.S. Pat. No. 4,772,714.

BACKGROUND OF THE INVENTION

The present invention relates to an α-substituted carbonyl compound and a process for the preparation of the same.

More particularly, the present invention relates to a process for the preparation of a ketone which is substituted with an aryl or heteroaryl group at the α-position, a novel α-azo ester having an azo group at the α-position and a process for the preparation thereof, and a novel α-hydrazono ester having a hydrazono group at the α-position and a process for the preparation thereof.

A ketone which is substituted with an aryl or heteroaryl group at the α-position is important as an intermediate for the synthesis of various pharmaceuticals or agricultural chemicals.

Up to this time, the introduction of an aryl group into the α-position of a ketone has been carried out by, for example, a method which comprises reacting a silyl enol ether of α-haloketone with an aryl copper or aryl nikel, a method which comprises reacting a potassium enolate of a ketone with a halogenated aryl compound under irradiation with light, a method which comprises reacting a sulfonylazoolefin with an aryl copper, a method which comprises reacting an α-haloketone with phenylborane, a method which comprises reacting hexadienilium iron with a silyl enol ether, a method which comprises reacting an enol ester of a ketone with phenyl mercury in the presence of a palladium catalyst or a method which comprises reacting a vinyl thio ether with bromobenzene in the presence of a palladium catalyst.

However, these methods have some disadvantages in, for example, that the yield is low, that the raw material is difficultly available or that the method itself lacks generality.

Recently, a method which comprises reacting a tin enolate of a ketone produced in situ with an aryl bromide in the presence of a palladium catalyst has been found. However, this method has disadvantages in that expensive reagents such as a palladium catalyst or a tin compound are required, that the separation of the product and the recovery of the palladium catalyst and residual tin need complicated operations and that the yield is not always satisfactory.

Under these circumstances, the inventors of the present invention have investigated how to introduce an aryl or heteroaryl group into the α-position of a ketone under mild conditions in a high yield and surprisingly have found that a diazonium salt reacted with a silyl enol ether to give a ketone which was substituted with an aryl or heteroaryl group at the α-position along with the release of nitrogen molecule. The present invention has been accomplished on the basis of this finding.

Up to this time, the reaction between a diazonium salt and a nucleophilic reagent (for example, Grignard reagent, alkyl enol ether or lithium enolate) has been thought to give an azo or hydrazono compound as a product without the release of nitrogen molecule. Consequently, the process for the preparation of a ketone which is substituted with an aryl or heteroaryl group at the α-position according to the present invention is a novel one which can not be expected from the prior art.

The α-azo ester and α-hydrazono ester according to the present invention are each useful as an intermediate for the synthesis of an α-amino acid.

α-amino acids and their derivatives are important chemicals which are now used in sweetener, seasoning, food additive, pharmaceuticals, agricultural chemicals, surfactant or the like as such or as a raw material and the demand for which is expected to increase with the development of biotechnology.

Although some α-amino acids can be prepared by a fermentation method using a microbe, the kind of amino acids which can be thus prepared are limited and not all amino acids can be obtained by fermentation.

Although the Strecker process using an aldehyde containing one less carbon atom is industrially employed as an organic synthesis method for an amino acid, this method requires hydrogen cyanide which is highly toxic and becomes more expensive with a decrease in the amount of hydrogen cyanide generated as a by-product in the Sohio process due to improvements in this method.

Alternatively, the Wakamatsu process which comprises the carbonylation between an amide and an aldehyde is known. But this process requires conditions of high temperature and high pressure. Further, the aldehyde to be used in the Strecker or Wakamatsu process is not always easy to come to hand. Furthermore, a reductive amination method of an α-keto acid is known but no industrially advantageous methods for preparing an α-keto acid have been developed. In addition to these methods, a method which comprises aminating a carboxylic ester at the α-position is also known. According to this method, a nitrogen atom is introduced into the α-position with ammonia, phthalimide, succinimide, sodium azide or the like, after halogenation of the ester at the α-position. However, this method has disadvantages in that the yield is not always high and that a relatively high temperature is required in the nucleophilic replacement step of a halogenated ester. As described above, methods of the prior art for the preparation of an α-amino acid or its intermediate have each disadvantages.

In view of these facts, the inventors of the present invention have investigated how to introduce an amino group or a functional group which can be converted into an amino group into the α-position of an ester and have found that a diazonium salt can be easily reacted with a ketene silyl acetal, which can be easily prepared from an ester, while releasing no nitrogen molecule, to give an azo compound or a hydrazo compound as a product. The present invention which relates to a novel α-azo ester or α-hydrazono ester or a process for the preparation thereof has been accomplished on the basis of this finding.

Up to this time, it has been thought that the reaction of a lithium enolate of an ester with a diazonium salt gives an α-azo compound and an α-hydrazono ester only in a very low yield. Consequently, the above finding can not be expected at all.

SUMMARY OF THE INVENTION

A first object of the present invention is to provide an α-substituted carbonyl compound and a process for the preparation thereof.

A second object of the present invention is to provide a process for the preparation of a ketone which is substituted with an aryl or heteroaryl group at the α-position.

A third object of the present invention is to provide a novel α-azo ester.

A fourth object of the present invention is to provide a process for the preparation of an α-azo ester.

The fifth object of the present invention is to provide a novel α-hydrazono ester.

A sixth object of the present invention is to provide a process for the preparation of a α-hydrazono ester.

PREFERRED EMBODIMENTS OF THE INVENTION

A process for the preparation of an α-substituted carbonyl compound according to the present invention is generally represented by the reaction formula (I):

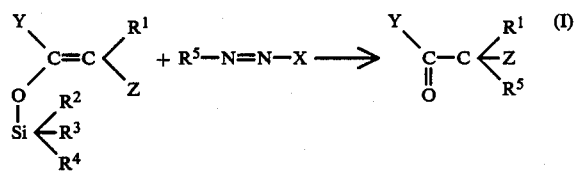

A process represented by the reaction formula (I), wherein Y is $R^6$ and Z is $R^7$, can be represented by the following reaction formula (II). More particularly, a silyl enol ether represented by the general formula (1) is reacted with a diazonium salt represented by the general formula (2) to yield a ketone which is substituted with an aryl or heteroaryl group at the α-position represented by the general formula (3):

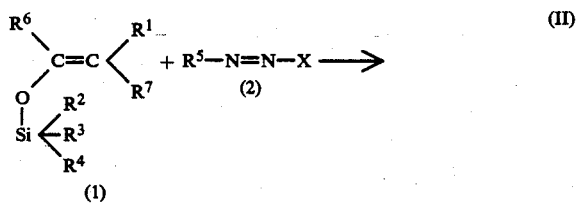

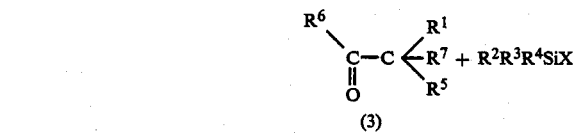

Further, a process represented by the reaction formula (I), wherein Y is $OR^8$ and Z is $R^7$, can be represented by the reaction formula (III). More precisely, a ketene silyl acetal represented by the general formula (4) is reacted with a diazonium salt (2) to give an α-azo ester represented by the general formula (5) as an α-substituted compound:

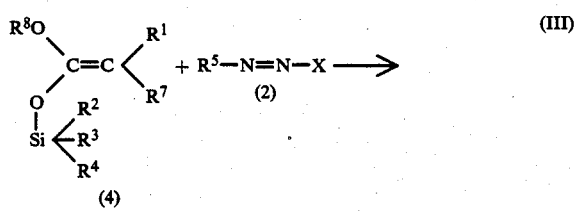

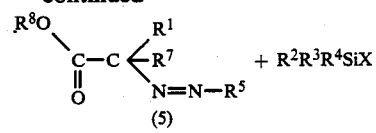

Furthermore, a process represented by the reaction formula (I), wherein Y is $R^6O$ and Z is H, can be represented by the reaction formula (IV). More specifically, a ketene silyl acetal represented by the general formula (6) is reacted with a diazonium salt (2) to afford an α-hydrazono ester represented by the general formula (7) as an α-substituted carbonyl compound.

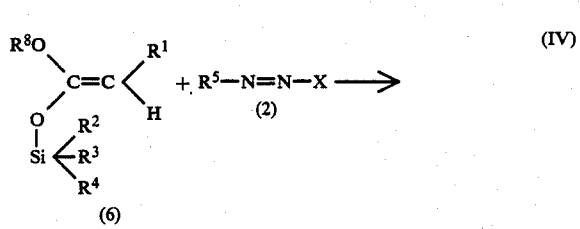

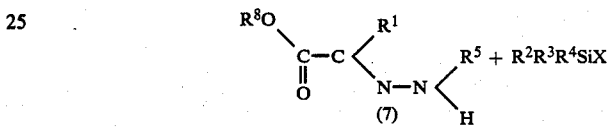

Now, each of the present invention methods will be described in more detail.

A: Process for the preparation of a ketone which is substituted with an aryl or heteroaryl group at the α-position [Reaction formula (II)]

In the general formula (1) representing a silyl enol ether, $R^1$, $R^6$ and $R^7$ are each a hydrogen atom or an organic substituent and $R^2$, $R^3$ and $R^4$ are each an alkyl, aryl or aralkyl group.

In the general formula (2) representing a diazonium salt, $R^5$ is an aryl or heteroaryl group and X is a diazonium salt-forming anion.

Although the silyl enol ether (1) to be used in this process may be any one, preferred examples thereof are compounds represented by the general formula (1) wherein the substituents $R^1$, $R^6$ and $R^7$ are each an alkyl, aralkyl, aryl, alkenyl, alkynyl or heteroaryl group and the substituents $R^2$, $R^3$ and $R^4$ are each an alkyl, aryl or aralkyl group, or $R^6$ and $R^1$ or $R^6$ and $R^7$ together form a ring structure.

These substituents will be described in more detail.

Examples of the alkyl group include $C_{1-8}$ alkyl groups such as methyl, ethyl, propyl, hexyl and octyl groups and those of the aralkyl group include benzyl and α- or β-phenylethyl groups. Examples of the aryl group include phenyl, tolyl, xylyl and naphthyl groups and those of the alkenyl group include vinyl, propenyl, butenyl, allyl, octenyl and styryl groups. Examples of the alkynyl group include ethynyl and phenylethynyl groups and those of the heteroaryl group include furyl, thiazolyl, thienyl and pyridyl groups. Further, these substituents may contain a functional group such as a halogen atom or an alkoxy, alkoxycarbonyl, dialkylamino, β-indolyl, dialkoxymethyl, thioalkoxy, nitro or cyano group.

The diazonium salt to be used in this process is not limited at all. Preferred examples thereof include any combination of $R^5$ and X as represented by the general formula (2) wherein the substituent $R^5$ is an aryl or heteroaryl group and X is a diazonium salt-forming anion, for example, a residue obtained by removing a hydrogen atom from an inorganic or organic acid or a diazonium salt-stabilizing complex ion represented by the general formula $1/1\ M_m Y_n$ (wherein M is a metal cation, Y is a halogen or cyanide ion, and l, m and n are each a natural number). Examples of the substituent $R^5$ include phenyl, chlorophenyl, bromophenyl, nitrophenyl, tolyl, anisyl, formylphenyl, ethoxycarbonylphenyl, dimethoxymethylphenyl, naphthyl, pyridyl, furyl and thienyl groups. Further, compounds having two diazonium moieties per molecule, such as 4,4'-biphenylene bisdiazonium salt, are preferably used.

Examples of the X in the general formula (2) include Cl, $HSO_4$, $NO_3$, $ClO_4$, $BF_4$, $BPh_4$, $PF_6$, $CH_3CO_2$, ½ $ZnCl_4$, ⅕ $SnCl_5$, ½ $HgCl_4$, ½ $CdCl_4$, ⅙ $Fe(CN)_6$ and $FeCl_4$.

The amount of the diazonium salt (2) used may be equal to or in slight excess of the equivalent of the silyl enol ether (1). Even if the amount is outside this range, the reaction will not be hindered.

The solvent to be used in this process represented by the reaction formula (II) may be any ordinary solvent except those which have an active proton source and are reactive with the silyl enol ether (1) or the diazonium salt (2), such as water, alcohols, phenols, carboxylic acids or primary or secondary amines. Examples of the solvent to be used include hexane, benzene, toluene, acetonitrile, pyridine, tetrahydrofuran, diethyl ether, acetone, dimethylformamide, sulfolane, ethyl acetate and Hexamethyl phosphorous triamide, among which pyridine is the most preferred. Further, these solvents may be used in admixture.

Although the reaction represented by the reaction formula (II) is generally carried out at a temperature of $-50°$ to $+50°$ C., it may be carried out under heating to a temperature higher than $+50°$ C. to attain a desired reaction rate depending upon the kinds of the silyl enol ether (1) and the diazonium salt (2).

The separation and purification of the objective ketone (3) which is substituted with an aryl or heteroaryl group at the α-position from the reaction mixture can be carried out by removing the diazonium salt from the reaction mixture by, for example, washing with water, removing the solvent by, for example, distillation and purifying the obtained residue by distillation, recrystallization, chromatography or the like.

As described above, the process represented by the reaction formula (II) for the preparation of a ketone which is substituted with an aryl or heteroaryl group at the α-position according to the present invention is advantageous in that a variety of silyl enol ethers (1) or diazonium salts (2) can be used so that various ketones which are substituted with an aryl or heteroaryl group at the α-position can be easily prepared in a high yield.

B: Novel α-azo ester (5) and process for the preparation thereof [Reaction formula (III)]

Examples of the novel α-azo ester (5) which can be prepared by the process represented by the reaction formula (III) include the following compounds:

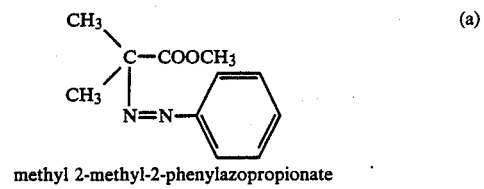

methyl 2-methyl-2-phenylazopropionate

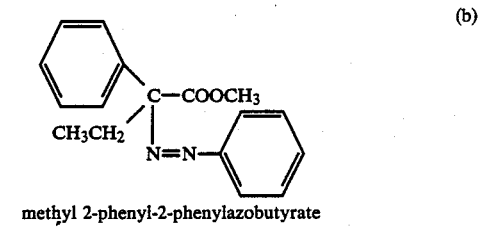

methyl 2-phenyl-2-phenylazobutyrate

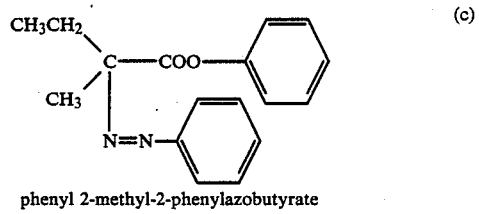

phenyl 2-methyl-2-phenylazobutyrate

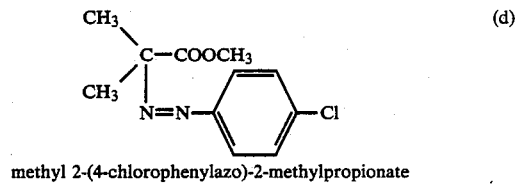

methyl 2-(4-chlorophenylazo)-2-methylpropionate

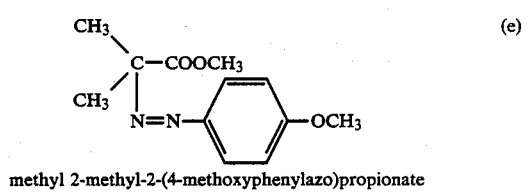

methyl 2-methyl-2-(4-methoxyphenylazo)propionate

In the general formulas (4) and (5) of the reaction formula (III), $R^1$ and $R^7$ are each an organic substituent and $R^2$, $R^3$, $R^4$ and $R^8$ are each an alkyl, aryl or aralkyl group. Further, in the general formulas (2) and (5), $R^5$ is an aryl or heteroaryl group and X is a diazonium salt-forming anion.

The organic substituents $R^1$ and $R^7$ are each as defined in the above paragraph A and so are the substituents $R^2$, $R^3$ and $R^4$. Further, the examples thereof are each the same as the ones described in the paragraph A.

$R^8$ is an alkyl, aryl or aralkyl group and the examples thereof are the same as the ones described in the paragraph A with respect to $R^2$, $R^3$ or $R^4$.

Further, examples of the X of the diazonium salt (2) and the amount of the diazonium salt (2) based on the ketene silyl acetal (4) are each the same as the ones described in the paragraph A.

Although the reaction represented by the reaction formula (III) generally proceeds under a mild condition of a temperature of $-30°$ C. to a room temperature, it may be carried out, if necessary, under heating to attain a desired reaction rate. However, too high a reaction temperature causes the decomposition of the diazonium salt, which is not preferred.

The solvent to be used in this process may be the same as the one described in the paragraph A except ones which are reactive with the ketene silyl acetal (4) or the diazonium salt (2).

Furthermore, the separation and purification of the obtained α-azo ester (5) can be carried out in a similar manner as the one described in the paragraph A with respect to the ketone (3).

As described above, the process represented by the reaction formula (III) for the preparation of an α-azo ester according to the present invention is advantageous in that a variety of ketene silyl acetals and diazonium salts can be used as a raw material so that various α-azo ester can be obtained by simple operations in a high yield.

C: Novel α-hydrazono ester (7) and process for the preparation thereof [Reaction formula (IV)]

Examples of the novel α-hydrazono ester (7) prepared by the process represented by the reaction formula (IV) include the following compounds:

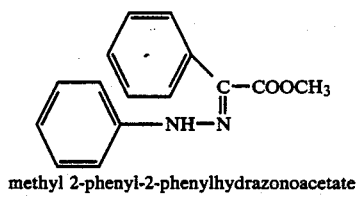

methyl 2-phenyl-2-phenylhydrazonoacetate

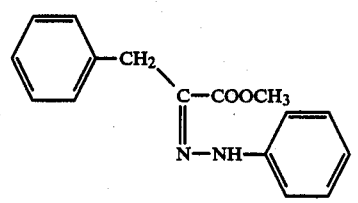

methyl 3-phenyl-2-phenylhydrazonopropionate

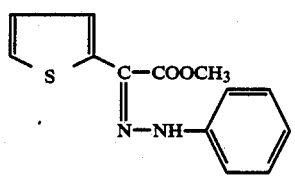

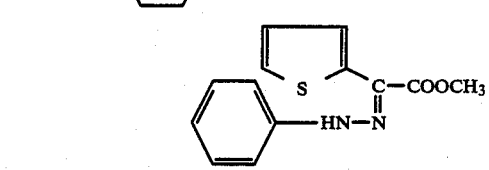

methyl 2-phenylhydrazono-2-(2-thienyl)acetate

In the general formulas (6) and (7) representing the ketene silyl acetal and α-hydrazono ester, respectively, in the reaction formula (IV), $R^1$, $R^2$, $R^3$ and $R^4$ are each as defined in the paragraph A. In the general formulas (2) and (7), $R^5$ is also as defined in the paragraph A.

Further, $R^8$ is an alkyl, aryl or aralkyl group and the X in the general formula (2) is as defined in the paragraph A.

Furthermore, examples of these substituents are also the same as the ones described in the paragraph A.

The amount of the diazonium salt (2) used and the reaction temperature are each the same as those described in the paragraph B. The solvent to be used in this process may be the same as the one described in the paragraph B except those which are reactive with the ketene silyl acetal (6) or diazonium salt (2). Additionally, the separation and purification of the objective α-hydrazono ester (7) from the reaction mixture can be carried out in a similar manner as the one described in the paragraph B.

As described above, the process represented by the reaction formula (IV) for the preparation of the α-hydrazono ester according to the present invention is advantageous in that a variety of ketene silyl acetals and diazonium salts can be used as a raw material so that various α-hydrazono esters can be prepared by simple operations in a high yield.

Examples of the present invention will now be described.

EXAMPLE 1

0.97 mmol of (1-phenylethenyl)oxytrimethylsilane was placed in a 20-ml flask, followed by the addition of 3 ml of pyridine as a solvent. 1.3 mmol of benzenediazonium tetrafluoroborate was added to the flask. The resulting mixture was stirred at 0° C. in a nitrogen atmosphere for 2 hours. The reaction mixture was diluted with diethyl ether and washed with 1.5N hydrochloric acid, water and a saturated aqueous solution of common salt, successively. The organic phase was dried over magnesium sulfate and distilled under a reduced pressure to remove the solvent. The obtained oily mixture was subjected to silica gel thin-layer chromatography to obtain 0.68 mmol of benzyl phenyl ketone.

The results are shown in Table 1.

EXAMPLES 2 TO 10

The same procedure as in Example 1 was repeated except that combinations of a silyl enol ether, a diazonium salt and a solvent given in Table 1 were each used. The results are shown in Table 1.

TABLE 1

| Ex. No. | Silyl enol ether (1) | Diazonium salt (2) | Solvent | Ketone (3) | Yield (%) |
|---|---|---|---|---|---|
| 1 | OSiMe₃ / Ph (as shown) | $C_6H_5N_2 \cdot BF_4$ | Pyridine | $PhCOCH_2Ph$ | 72 |
| 2 | OSiMe₃ / Ph (as shown) | $p\text{-}ClC_6H_4N_2 \cdot BF_4$ | Pyridine | $PhCOCH_2\text{-}C_6H_4\text{-}Cl$ | 73 |

TABLE 1-continued

| Ex. No. | Silyl enol ether (1) | Diazonium salt (2) | Solvent | Ketone (3) | Yield (%) |
|---|---|---|---|---|---|
| 3 | $\text{Ph}\underset{}{\overset{\text{OSiMe}_3}{\diagup}}$ | $p\text{CH}_3\text{OC}_6\text{H}_4\text{N}_2\cdot\text{BF}_4$ | Pyridine | $\text{PhCOCH}_2\text{—C}_6\text{H}_4\text{—OMe}$ | 65 |
| 4 | 2-(1-(trimethylsilyloxy)vinyl)thiophene | $\text{PhN}_2\cdot\text{BF}_4$ | Pyridine | 2-thienyl–CO–CH$_2$Ph | 58 |
| 5 | 2-(1-(trimethylsilyloxy)vinyl)furan | $\text{PhN}_2\cdot\text{BF}_4$ | Pyridine | 2-furyl–CO–CH$_2$Ph | 47 |
| 6 | Ph–C(OSiMe$_3$)=CH–CH$_3$ | $\text{PhN}_2\cdot\text{BF}_4$ | Pyridine | Ph–CO–CH(CH$_3$)(Ph) | 71 |
| 7 | C$_7$H$_{15}$–C(OSiMe$_3$)=CH$_2$ | $\text{PhN}_2\cdot\text{BF}_4$ | Pyridine | C$_7$H$_{15}$–CO–CH$_2$Ph | 31 |
| 8 | Ph–C(OSiMe$_3$)=CH$_2$ | $\text{PhN}_2\cdot\text{BF}_4$ | HMPA | Ph–CO–CH$_2$Ph | 9 |
| 9 | Ph–CH$_2$–C(OSiMe$_3$)=CH–Ph | $\text{PhN}_2\cdot\text{BF}_4$ | Pyridine | Ph–CH$_2$–CO–CH(Ph)$_2$ | 4 |
| 10 | Ph–C(OSiMe$_3$)=CH$_2$ | $\text{PhN}_2\text{Cl}$ | Pyridine | PhCOCH$_2$Ph | 2 |

EXAMPLE 11

1.0 mmol of (1-methoxy-2,2-dimethylethenyl)oxytrimethylsilane was placed in a 20-ml flask, followed by the addition of 3 ml of pyridine as a solvent. 1.3 mmol of benzenediazonium tetrafluoroborate was added to the flask. The obtained mixture was stirred at 0° C. in a nitrogen atmoshere for 2 hours. The reaction mixture was diluted with diethyl ether and washed with 1.5N hydrochloric acid, water and a saturated aqueous solution of common salt successively. The obtained organic phase was dried over magnesium sulfate and distilled under a reduced pressure to remove the solvent. The obtained oily mixture was subjected to silica gel thin-layer chromatography to obtain 0.90 mmol of methyl 2-methyl-2-phenylazopropionate.

Results of elemental analysis and infrared or NMR spectroscopic analysis thereof are shown in Table 2.

EXAMPLES 12 to 24

The same procedure as in Example 11 was repeated except that combinations of a ketene silyl acetal, a diazonium salt and a solvent given in Table 2 were each used. The results are shown in Table 2.

TABLE 2

| Ex. No. | Ketene silyl acetal [mixture of (E) and (Z)] | Diazonium salt | Solvent | Product (Oil) | Yield (%) | Elemental analysis observed | Elemental analysis calculated | IR spectrum (neat) | NMR spectrum (CDCl₃, δ) |
|---|---|---|---|---|---|---|---|---|---|
| 11 | Me\OMe, Me/OSiMe₃ | PhN₂BF₄ | Pyridine | Me-C(CO₂Me)(Me)-N₂Ph | 90 | C 63.91 H 6.83 N 13.38 | 64.04 6.84 13.58 | 1740 (CO₂Me) | 1.59(S, 6H, Me₂C) 3.71(S, 3H, CO₂Me) 7.3–7.8(m, 5H, Ph) |
| 12 | " | Cl-C₆H₄-N₂BF₄ | " | Me-C(CO₂Me)(Me)-N₂-C₆H₄Cl | 72 | C 54.80 H 5.36 N 11.90 | 54.89 5.44 11.64 | 1744 (CO₂Me) | 1.57(S, 6H, Me₂C) 3.74(S, 3H, CO₂Me) 7.43(d, J=9Hz, 2H, C₆H₄Cl) 7.70(d, J=9Hz, 2H, C₆H₄Cl) |
| 13 | " | MeO-C₆H₄-N₂BF₄ | " | Me-C(CO₂Me)(Me)-N₂-C₆H₄-OMe | 84 | C 60.78 H 6.74 N 11.63 | 61.00 6.83 11.86 | 1742 (CO₂Me) | 1.56(S, 6H, Me₂C) 3.73(S, 3H) 3.82(S, 3H) →(CO₂Me or MeOC₆H₄) 6.93(d, J=9Hz, 2H, MeOC₆H₄) 7.72(d, J=9Hz, 2H, MeOC₆H₄) |
| 14 | Ph\OMe, Et/OSiMe₃ | PhN₂BF₄ | " | Ph-C(CO₂Me)(Et)-N₂Ph | 90 | C 72.06 H 6.41 N 9.97 | 72.32 6.43 9.92 | 1740 (CO₂Me) | 0.83(t, J=7Hz, 3H, Et) 2.43(q, J=7Hz, 2H, Et) 3.65(S, 3H, CO₂Me) 7.2–8.0(m, 10H, Ph) |
| 15 | Et\OPh, Me/OSiMe₂Ph | " | " | Et-C(CO₂Ph)(Me)-N₂Ph | 90 | C 72.18 H 6.33 N 9.84 | 72.32 6.43 9.92 | 1760 (CO₂Ph) | 1.13(t, J=8Hz, 3H, Et) 1.65(S, 3H, MeO) 2.30(q, J=8Hz, 2H, Et) 7.0–8.0(m, 10H, Ph) |
| 16 | Me\OMe, Me/OSiMe₃ | " | THF | Me-C(CO₂Me)(Me)-N₂Ph | 88 | Same as Experiment 11 | | | |
| 17 | " | " | collidine | " | 82 | | | | |
| 18 | " | " | CH₃CN | " | 85 | | | | |
| 19 | " | " | DMF | " | 80 | | | | |
| 20 | " | " | CH₂Cl₂ | " | 68 | | | | |
| 21 | " | " | HMPA | " | 52 | | | | |
| 22 | " | " | toluene | " | 51 | | | | |
| 23 | PhCH₂\OMe, Me/OSiMe₃ | PhN₂BF₄ | Pyridine | PhCH₂-C(CO₂Me)(Me)-N₂Ph | 80 | C 72.16 H 6.30 N 9.95 | 72.32 6.43 9.92 | 1740 (CO₂Me) | 3.85(S, 3H, CO₂Me) 3.50(S, 2H, CH₂) 7.0–8.0(m, 10H, Ph) |

Note:
THF: tetrahydrofuran
DMF: dimethylformamide
HMPA: hexamethylphosphorous triamide

TABLE 2-continued
| Ex. No. | Ketene silyl acetal [mixture of (E) and (Z)] | Diazonium salt | Solvent | Product (Oil) | Yield (%) | Elemental analysis observed calculated | IR spectrum (neat) | NMR spectrum (CDCl$_3$, δ) |
|---|---|---|---|---|---|---|---|---|
| 24 |  | PhN$_2$BPh$_4$ | " | Ph$-$C(CO$_2$Me)(Et)(N$_2$Ph) | 53 | Same as Experiment 14 | | |

EXAMPLE 25

1.0 mmol of (1-methoxy-2phenylethenyl)oxytrimethylsilane was placed in a 20-ml flask, followed by the addition of 3 ml of pyridine as a solvent. 1.3 mmol of benzenediazonium tetrafluoroborate was added to the flask. The obtained mixture was stirred at 0° C. in a nitrogen atmosphere for 2 hours. The reaction mixture was diluted with diethyl ether and washed with 1.5N hydrochloric acid, water and a saturated aqueous solution of common salt successively. The obtained organic phase was dried over magnesium sulfate and distilled under a reduced pressure to remove the solvent. The obtained oily mixture was subjected to silica gel thin-layer chromatography to obtain 0.84 mmol of methyl 2-phenyl-2-phenylhydrazonoacetate.

Results of elemental analysis and infrared or NMR spectroscopic analysis thereof are shown in Table 3.

EXAMPLES 26 to 32

The same procedure as in Example 25 was repeated except that combinations of a ketene silyl acetal and a solvent given in Table 3 were each used. The results are shown in Table 3.

TABLE 3

| Ex. No. | Ketene silyl acetal [mixture of (E) and (Z)] | Diazonium salt | Solvent | Product | Yield (%) | Elemental analysis observed | Elemental analysis calculated | IR spectrum | NMR spectrum (CDCl$_3$, δ) |
|---|---|---|---|---|---|---|---|---|---|
| 25 | Ph—C(OMe)=C(OSiMe$_3$) | PhN$_2$BF$_4$ | Pyridine | Ph—C(CO$_2$Me)=N—NH—Ph<br>m.p. 118–119 | 73 | C 70.71<br>H 5.52<br>N 10.90 | 70.85<br>5.55<br>11.02 | KBr 1714 (CO$_2$Me) | 3.85(S, 3H, CO$_2$Me)<br>6.8–7.8(m, 10H, Ph)<br>8.15(br S, 1H, NH) |
| 26 | PhCH$_2$—C(OMe)=C(OSiMe$_3$) | ″ | ″ | PhCH$_2$—C(CO$_2$Me)=N—NH—Ph<br>m.p. 87–89 | 76 | C 71.56<br>H 6.04<br>N 10.27 | 71.62<br>6.01<br>10.44 | CHCl$_3$ 1706 (CO$_2$Me) | 3.88(S, 3H, CO$_2$Me)<br>4.06(S, 2H, CH$_2$)<br>6.8–7.4(m, 10H, Ph)<br>8.09(brs, 1H, NH) |
| 27 | thienyl—C(OMe)=C(OSiMe$_3$) | ″ | ″ | thienyl—C(CO$_2$Me)=N—NH—Ph<br>m.p. 85–86 | 65 | C 59.91<br>H 4.64<br>N 10.61 | 59.98<br>4.65<br>10.76 | CHCl$_3$ 1710 (CO$_2$Me) | 3.86(S, 3H, CO$_2$Me)<br>6.8–7.7(m, 8H, thienyl, Ph)<br>8.73(br S, 1H, NH) |
|  |  |  |  |  | 7 | C 59.89<br>H 4.61<br>N 10.62 | 59.98<br>4.65<br>10.76 | CHCl$_3$ 1684 (CO$_2$Me) | 3.95(S, 3H, CO$_2$Me)<br>6.8–7.6(m, 8H, thienyl, Ph)<br>12.5(br S, 1H, NH) |
| 28 | Ph—C(OMe)=C(OSiMe$_3$) | ″ | THF | Ph—C(CO$_2$Me)=N—NHPh<br>m.p. 77–78 | 88 | Same as Example 23 |  |  |  |
| 29 | ″ | 4-MeO-C$_6$H$_4$-N$_2$ BF$_4$ | CH$_3$CN | ″ | 63 |  |  |  |  |
| 30 | Me—C(OMe)=C(OSiMe$_3$) | ″ | Pyridine | Me—C(CO$_2$Me)=N—NH—C$_6$H$_4$—OMe | 82 | C 63.95<br>H 6.80<br>N 13.42 | 64.06<br>6.84<br>13.58 | 1705 (CO$_2$Me) | 2.03(S, 3H, CH$_3$)<br>3.73(S, 3H, CH$_3$O)<br>3.83(S, 3H, CH$_3$O)<br>6.92(d, J=9H$_z$, 2H, Ar)<br>7.72(d, J=9H$_z$, 2H, Ar) |

TABLE 3-continued

| Ex. No. | Ketene silyl acetal [mixture of (E) and (Z)] | Diazonium salt | Solvent | Product | Yield (%) | Elemental analysis observed | Elemental analysis calculated | IR spectrum | NMR spectrum (CDCl$_3$, δ) |
|---|---|---|---|---|---|---|---|---|---|
| 31 | Ph⟶OPh / OSiMe$_2$Ph | PhN$_2$BF$_4$ | " | Ph⟶CO$_2$Ph, H, PhN—N | 76 | C 75.67 H 5.03 N 8.64 | 75.93 5.10 8.85 | 1730 (CO$_2$Me) | 7.0–8.0(m, 15H, Ph) 8.15 (br S, 1H, NH) |
| 32 | Ph⟶OMe / OSiMe$_3$ | PhN$_2$BPh$_4$ | Toluene | Ph⟶CO$_2$Me, H, PhN—N | 23 | Same as Experiment 23 | | | |

What is claimed is:

1. A process for the preparation of an α-hydrazono ester represented by the formula (7), which comprises reacting a ketene silyl acetal represented by the formula (6) with a diazonium salt represented by the formula (2):

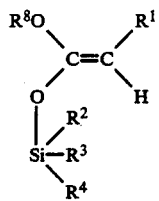  (6)

  (2)

  (2)

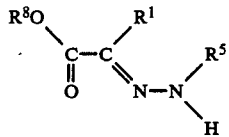  (7)

wherein $R^1$ is a member selected from the group consisting of $C_{1-8}$ alkyl, $C_{7-8}$ aralkyl, $C_{6-10}$ aryl, $C_{2-8}$ alkenyl, $C_{2-8}$ alkynyl, $C_{3-5}$ heteroaryl and substituted derivatives thereof containing a substituent selected from the group consisting of halogen, alkoxy, alkoxycarbonyl, dialkylamino, β-indolyl, dialkoxymethyl, thioalkoxy, nitro and cyano; each of $R^2$, $R^3$, $R^4$ and $R^8$ is a member independently selected from the group consisting of the above alkyl, aryl and aralkyl; $R^5$ is a member selected from the group consisting of phenyl, chlorophenyl, bromophenyl, nitrophenyl, tolyl, anisyl, formylphenyl, ethoxycarbonylphenyl, dimethoxymethylphenyl, naphthyl, pyridyl, furyl, thienyl and 4,4′-biphenylenyl; and X is a member selected from the group consisting of Cl, $HSO_4$, $NO_3$, $ClO_4$, $BF_4$, $B(C_6H_5)_4$, $PF_6$, $CH_3CO_2$, ½ $ZnCl_4$, ½ $SnCl_6$, ½ $HgCl_4$, ½ $CdCl_4$, ⅓ $Fe(CN)_6$ and $FeCl_4$.

2. A process for the preparation of an α-hydrazono ester as set forth in claim 1, wherein the aralkyl group is benzyl, α-phenylethyl or β-phenylethyl group.

3. A process for the preparation of an α-hydrazono ester as set forth in claim 1, wherein the aryl groups of $R^1$, $R^2$, $R^3$, $R^4$ and $R^8$ are each phenyl, tolyl, xylyl or naphthyl group.

4. A process for the preparation of an α-hydrazono ester as set forth in claim 1, wherein said alkenyl group is vinyl, propenyl, butenyl, allyl, octenyl or styryl group.

5. A process for the preparation of an α-hydrazono ester as set forth in claim 1, wherein said alkynyl group is ethynyl or phenylethynyl group.

6. A process for the preparation of an α-hydrazono ester as set forth in claim 1, wherein said heteroaryl is a furyl, thiazolyl, thienyl or pyridyl group.

* * * * *